(12) United States Patent
Long et al.

(10) Patent No.: US 10,919,826 B2
(45) Date of Patent: Feb. 16, 2021

(54) PROCESS FOR THE CONVERSION OF SYNTHESIS GAS TO ISOBUTANOL

(71) Applicants: CHINA PETROLEUM & CHEMICAL CORPORATION, Beijing (CN); UOP LLC, Des Plaines, IL (US)

(72) Inventors: Richard Long, Katy, TX (US); Tian Ruan, Katy, TX (US); Lubo Zhou, Deer Park, IL (US); Jinbiao Guo, Katy, TX (US)

(73) Assignees: China Petroleum & Chemical Corporation, Beijing (CN); UOP LLC, Des Plaines, IL (US)

( * ) Notice: Subject to any disclaimer, the term of this patent is extended or adjusted under 35 U.S.C. 154(b) by 0 days.

(21) Appl. No.: 16/593,256

(22) Filed: Oct. 4, 2019

(65) Prior Publication Data

US 2020/0039905 A1   Feb. 6, 2020

Related U.S. Application Data

(63) Continuation of application No. PCT/US2018/020260, filed on Feb. 28, 2018.

(51) Int. Cl.
*C07C 29/34* (2006.01)
*C07C 31/12* (2006.01)

(52) U.S. Cl.
CPC .............. *C07C 29/34* (2013.01); *C07C 31/12* (2013.01)

(58) Field of Classification Search
CPC ........ C07C 29/34; C07C 29/151; C07C 31/12
See application file for complete search history.

(56) References Cited

U.S. PATENT DOCUMENTS

| 2,564,130 | A |   | 8/1951  | Schreyer |
|-----------|---|---|---------|----------|
| 4,122,110 | A | * | 10/1978 | Sugier ...................... B01J 23/78 502/306 |
| 4,564,643 | A | * | 1/1986  | Shibata ..................... B01J 23/76 518/714 |
| 4,661,525 | A | * | 4/1987  | Grazioso ............... C07C 29/156 502/206 |
| 5,300,695 | A | * | 4/1994  | Radlowski .............. C07C 29/32 568/697 |

(Continued)

FOREIGN PATENT DOCUMENTS

| BR | 10700631 A  | 10/2008 |
|----|-------------|---------|
| CN | 103272609 A | 9/2013  |
| EP | 0208102 A2  | 1/1987  |

OTHER PUBLICATIONS

Keim, E. et al., Isobutanol from synthesis gas, Cataysis Letters, 3, pp. 59-64 (Year: 1989).*

(Continued)

*Primary Examiner* — Yate' K Cutliff (57) ABSTRACT

An improved isobutanol synthesis process is provided which proceeds through the formation of mixed alcohols from syngas. The two-step process avoids the slowest α-carbon addition reaction in the conventional one-step, direct isobutanol synthesis process. Once ethanol and propanol are produced in the first reaction zone, they can react with methanol and/or syngas in a second reaction zone to produce isobutanol through the fast β-carbon addition reaction in the presence of catalysts, resulting on significantly improved isobutanol productivity.

19 Claims, 4 Drawing Sheets

(56) References Cited

U.S. PATENT DOCUMENTS

| | | | |
|---|---|---|---|
| 5,493,064 A | | 2/1996 | Vanderspurt et al. |
| 5,559,275 A | * | 9/1996 | Barger .................. C07C 29/34 |
| | | | 568/403 |
| 5,658,843 A | * | 8/1997 | Tsukada .................. B01J 23/60 |
| | | | 502/344 |
| 5,691,268 A | | 11/1997 | Koveal et al. |
| 5,703,133 A | | 12/1997 | Vanderspurt et al. |
| 5,707,920 A | | 1/1998 | Vanderspurt et al. |
| 5,767,166 A | | 6/1998 | Antonelli et al. |
| 5,811,602 A | | 9/1998 | Vanderspurt et al. |
| 7,034,196 B2 | * | 4/2006 | Clem .................. B01J 8/1827 |
| | | | 585/638 |
| 7,078,578 B2 | * | 7/2006 | Janssens .................. B01J 29/40 |
| | | | 585/638 |
| 8,865,609 B2 | * | 10/2014 | Zhou .................. B01J 37/0244 |
| | | | 502/100 |
| 9,266,807 B1 | | 2/2016 | Norman et al. |
| 2009/0018371 A1 | * | 1/2009 | Klepper .............. C07C 29/1518 |
| | | | 568/902.2 |
| 2010/0317900 A1 | | 12/2010 | Daniel et al. |
| 2013/0035524 A1 | | 2/2013 | Orosco et al. |
| 2013/0252299 A1 | | 9/2013 | Bell et al. |

OTHER PUBLICATIONS

Joseph J. Maj, et al., Thorium Oxide: A New Catalyst for Methanol, Isobutanol, and Light Hydrocarbon Production from Carbon Monoxide and Hydrogen, Applied Catalysis, 10 (1984) 313-316.

Shaopeng Tian, et al., Cation Distribution in Zn—Cr Spinel Structure and its Effects on Synthesis of Isobutanol from Syngas: Structure-activity Relationship, Journal of Molecular Catalysis A: Chemical 404-405 (2015), 139-147.

Yingquan Wu, et al., Isobutanol Synthesis from Syngas Over K—Cu/ZrO2—La2O3(x) Catalysts: Effect of La-Loading, Journal of Molecular Catalysis A: Chemical 396 (2015) 254-260.

Ho Ting Luk et al., Status and Prospects in Higher Alcohols Synthesis from Syngas, Chem Soc Rev, Apr. 20, 2016.

Kozlowski, Joseph T., et al., Heterogeneous Catalysts for the Guerbert Coupling of Alcohols, American Chemical.Society, 1588-1600, 2013.

Kai A.N. Verkerk, et al., Recent Developments in Isobutanol Synthesis from Synthesis Gas, Applied Catalysis A: General 186 (1999) 407-431.

Xu Xiaoding, et al., Synthesis of Higher Alcohols from Syngas—Recently Patented Catalysts and Tentative Ideas on the Mechanism, Catalysis Today, 2 (1987) 125-170.

Written Opinion from PCT Application No. PCT/US2018/020260, dated Nov. 8, 2018.

International Search report from PCT Application No. PCT/US2018/020260, dated Nov. 8, 2018.

International Preliminary Report on Patentability from PCT Application No. PCT/US2018/020260, dated Sep. 1, 2020.

* cited by examiner

PROCESS FOR THE CONVERSION OF SYNTHESIS GAS TO ISOBUTANOL

This application is a continuation of PCT/2018/020260, entitled Process for the Conversion of Synthesis Gas to Isobutanol, filed Feb. 28, 2019, which is incorporated herein in its entirety.

BACKGROUND

Isobutanol is an organic solvent and a feedstock in the manufacturing of isobutyl acetate and isobutyl esters. It can also be blended directly with gasoline to improve octane number and combustion efficiency or used as a neat alternative fuel. Isobutanol has relatively higher energy density, and lower volatility compared to ethanol. In addition, it does not readily absorb water from air, preventing the corrosion of engines and pipelines. It also has a higher octane number than ethanol, resulting in less knocking in engines.

Although isobutanol has many potential uses, its synthesis is currently limited. Isobutanol can be produced through hydroformylation of propylene: a process involving reacting propylene with carbon monoxide and hydrogen to generate isobutyraldehyde and then hydrogenating the isobutyraldehyde to isobutanol. For example, U.S. Pat. No. 2,564,130 discloses a process for the manufacture of n-butanol and isobutanol from a mixture containing propylene, CO, and $H_2$ at 225-300° C. in the presence of a cobalt-containing catalyst. Although this hydroformylation process is currently used for manufacturing butanol, it is not energy efficient due to the high energy needed for production of propylene and synthesis gas (syngas). Further, when isobutanol is used as a gasoline additive, demand for it is expected to increase the demand for propylene significantly, leading to an increase in the cost of this process.

Alternatively, synthesis of isobutanol directly from more abundant and less-expensive syngas has been investigated extensively. The syngas, containing carbon monoxide and hydrogen, is mainly produced from reforming or partial oxidation of natural gas and light hydrocarbons, or gasification of coal and biomass at high temperatures. It can also be produced from gasification of municipal solid waste. The carbon monoxide and hydrogen react at high temperatures and high pressures to produce methanol and isobutanol on alkali promoted ZnO and CuO—ZnO based catalysts, with methane and light hydrocarbons as main by-products. For example, U.S. Pat. No. 5,767,166 discloses an isobutanol synthesis process from syngas in one reactor on alkali promoted Zn—Cr oxide catalysts. Under the conditions of 420° C., 18 MPa, $H_2$/CO molar ratio of 1.0, and gas hourly space velocity of 20,000 per hour, 165 g/kg-cat/h isobutanol was achieved. A similar process is disclosed in CN Pat. Pub. No. 103,272,609 in which 32-61% carbon monoxide conversions were obtained, with 25-45 wt % isobutanol in the liquid alcohols, on alkali and rare earth oxide promoted CuO—ZnO—ZrO$_2$ catalysts.

Although this direct isobutanol synthesis from syngas has been extensively investigated, it is often associated with poor isobutanol selectivity and productivity. During operation, lower temperature results in higher methanol selectivity, while higher temperature tends to produce more methane and light hydrocarbons. Consequently, high isobutanol selectivity and yield are difficult to achieve on the alkali promoted ZnO and CuO—ZnO catalysts.

Therefore, it would be desirable to have a process which can overcome the above obstacles and improve the isobutanol selectivity and productivity.

DETAILED DESCRIPTION

A new route to convert syngas (CO and $H_2$) to isobutanol through mixed alcohols is disclosed. The syngas can be produced from reforming or partial oxidation of natural gas and light hydrocarbons, or gasification of coal or biomass at high temperatures. It can also be produced from gasification of municipal solid waste. Therefore, this process can be applied to the processes of converting coal, natural gas, biomass, and/or waste to isobutanol.

One aspect of the invention is a carbon monoxide hydrogenation to isobutanol process. In one embodiment, the syngas is first converted to mixed alcohols, including but not limited to methanol, ethanol, and propanol on heterogeneous catalysts. Small amounts of isobutanol and/or higher alcohols may also be produced depending on the catalysts used. In some embodiments, the ethanol and propanol produced in the first reaction can react with methanol (from the first reaction or from another source) and/or syngas in a second reaction to produce at least an additional portion of isobutanol in the presence of catalysts. In some embodiments, the methanol from the first reaction can be converted to ethylene and propylene through a methanol-to-olefins process, or to gasoline through a methanol-to-gasoline process using heterogeneous catalysts.

Hydrogenation of carbon monoxide to isobutanol has been studied for over one hundred years. Although there are still some questions, many researchers believe that the isobutanol is formed in consecutive aldol-condensation reactions by carbon addition at either the β- or the α-carbon atom of the growing alcohol or aldehyde intermediate, as described in "Recent developments in isobutanol synthesis from synthesis gas," Appl. Catal. A 1999, 186, 407-431, which is incorporated herein by reference. In a simplified mechanism, CO and $H_2$ can react to form methanol/formaldehyde, which sequentially reacts with CO/$H_2$ to form ethanol/acetaldehyde intermediate. This step is called α-carbon addition, and it is considered the slowest, rate-determining step in the consecutive set of reactions leading to the formation of isobutanol. The ethanol/acetaldehyde formed then reacts with CO/$H_2$ to form propanol/propionaldehyde intermediate, which sequentially reacts with CO/$H_2$ to form isobutanol in the same catalyst bed. The last two steps, i.e., conversion of ethanol/acetaldehyde to propanol/propionaldehyde intermediate and subsequent isobutanol product, are called β-carbon addition. The β-carbon addition steps are much faster than the α-carbon addition step for the conversion of methanol/formaldehyde to ethanol/acetaldehyde. Because of its steric hindrance and the lack of the two β-hydrogens needed for aldol condensation reactions, isobutanol does not possess a high reactivity for further aldol-condensation reaction to produce higher alcohols. The aldol condensation stops at isobutanol. Consequently, isobutanol becomes a preferred end-product in the alcohol chain growth.

Methanol and isobutanol are the two main components in the alcohol products. Once ethanol and propanol are produced, they can react with $CO/H_2$ to form isobutanol quickly through the β-carbon addition reaction. Therefore, ethanol and propanol concentrations are always low for the direct isobutanol synthesis reaction on the alkali-promoted ZnO and CuO—ZnO catalysts.

Because methanol formation from syngas is fast but methanol consumption (i.e., α-carbon addition reaction) is slow, methanol formation in the isobutanol synthesis generally reaches thermal equilibrium under the reaction conditions. Its concentration in the product is related to the reaction temperature and pressure. As an intermediate, the methanol concentration will impact isobutanol productivity. However, the isobutanol productivity is mainly controlled by the reaction rate of the α-carbon addition, which is the slowest step during the formation of isobutanol from syngas.

Therefore, in order to increase isobutanol selectivity and productivity, the reaction rate of the α-carbon addition, i.e., methanol/formaldehyde-to-ethanol/acetaldehyde step, needs to be improved. A mild increase in reaction temperature can speed up the α-carbon addition and result in more isobutanol production on the isobutanol synthesis catalysts. In other words, operation at higher temperatures will favor isobutanol-to-methanol ratio. However, methanol formation, which generally reaches thermal equilibrium under the reaction conditions, decreases with increasing reaction temperature. Therefore, operation at higher temperatures will not favor methanol formation. Because methanol formation is necessary for the formation of higher alcohols, the decrease in its concentration at higher temperatures will reduce the production of higher alcohols. Moreover, higher temperatures also result in the formation of more undesired methane and light hydrocarbons. Consequently, high selectivity and yield toward isobutanol are hard to achieve in the direct isobutanol synthesis process from syngas.

It has been discovered that carbon monoxide can react with hydrogen to produce methanol, ethanol, propanol, and other mixed alcohols under mild conditions on some heterogeneous catalysts. It is generally accepted that this mixed alcohols synthesis occurs through a CHx ($1 \leq x \leq 2$) coupling and insertion mechanism for the chain growth rather than the aforementioned aldol-condensation mechanism (i.e., α- and β-carbon addition), as described in "Synthesis of higher alcohols from syngas—recently patented catalysts and tentative ideas on the mechanism," Catalysis Today, 2 (1987) 125-170. A substantial amount of ethanol and propanol are produced from the syngas in the reaction.

Therefore, an improved isobutanol synthesis process is provided through the formation of mixed alcohols. This new two-step process avoids the slowest α-carbon addition reaction (i.e., methanol/formaldehyde-to-ethanol/acetaldehyde) in the conventional one-step, direct isobutanol synthesis process. Once ethanol and propanol are produced in the first reaction zone, they can react with methanol and/or syngas in a second reaction zone to produce isobutanol through the fast Guerbet reaction and/or β-carbon addition reaction in the presence of catalysts. As a result, the isobutanol productivity will be improved significantly.

In one embodiment, the method comprises introducing synthesis gas into a first reaction zone in the presence of a first heterogeneous catalyst to produce a reaction mixture comprising a mixture of alcohols comprising: methanol, a substantial amount of ethanol and propanol, and possibly a small amount of higher alcohols (e.g., isobutanol); separating the reaction mixture into at least a first stream comprising the methanol, a second stream comprising the ethanol and propanol, and optionally a third stream comprising the isobutanol (if any); and introducing the synthesis gas and at least a portion of the second stream into a second reaction zone in the presence of a second heterogeneous catalyst to produce isobutanol. By a substantial amount of ethanol and propanol, we mean that the weight ratio of ethanol and propanol to methanol is greater than 0.2:1, or greater than 0.5:1, or greater than 1:1.

In some embodiments, a molar ratio of $H_2$ to CO in the synthesis gas is in a range of 10:1 to 0.1:1, or 5:1 to 0.2:1, or 2:1 to 0.5:1. In some embodiments, in addition to CO and $H_2$, $CO_2$ or an inert gas, such as $N_2$ and Ar, may also be present in the syngas.

In some embodiments, the first heterogeneous catalyst comprises one or more of Cu—Co containing catalysts, Cu—Fe containing catalysts, Cu—Ni containing catalysts, promoted Mo catalysts, and precious metal catalysts (for instance, gold, silver, platinum, palladium, ruthenium, rhodium, rhenium, osmium, or iridium containing catalyst), and combinations thereof.

In some embodiments, the reaction temperature in the first reaction zone could range from 200 to 450° C., or from 250 to 350° C. In some embodiments, the pressure in the first reaction zone could range from 10 to 200 atm (1.0 to 20.3 MPa), or from 50 to 150 atm (5.1 to 15.2 MPa).

In some embodiments, the reaction mixture is separated by distillation or an adsorption desorption process.

In some embodiments, the second heterogeneous catalyst comprises elements from Groups IA, IIA, IIIA, IV, IB, IIB, IIIB, VIB, VIIB, and VIIIB in the Periodic Table. In some embodiments, the second heterogeneous catalyst comprises alkali and alkaline earth promoted ZnO or CuO catalysts. For instance, the second heterogeneous catalyst may contain mixed oxides of K—Zn—Cr, K—Zn—Zr, K—Cu—Zn—Cr and K—Cu—Zn—Zr.

In some embodiment, the reaction temperature in the second reaction zone could be from 200 to 500° C., preferably from 250 to 450° C. In some embodiments, the pressure in the second reaction zone could be from 10 to 300 atm (1.01 to 30.4 MPa), or from 50 to 200 atm (5.1 to 20.3 MPa).

In some embodiments, the method includes introducing at least a portion of the first stream and at least a portion of the second stream to a third reaction zone in the presence of a third heterogeneous catalyst to produce a third portion of isobutanol.

In some embodiments, the method includes introducing synthesis gas into the third reaction zone.

In some embodiments, the third heterogeneous catalyst comprises elements from Groups IA, IIA, IIIA, IVA, VA, IV, IB, IIB, VIB, VIIB, and VIIIB in the Periodic Table, for instance, MgO, MgO—$Al_2O_3$, CuO—MgO—$Al_2O_3$, Ca—$PO_4$ and alkali zeolites. The reaction temperature in the third reaction zone could be from 100 to 500° C., or from 150 to 400° C. In some embodiments, the pressure in the third reaction zone could be from 1 to 300 atm (0.1 to 30.4 MPa), or from 1 to 100 atm (0.1 to 10.1 MPa).

In some embodiments, the method includes introducing at least a portion of the first stream into a methanol-to-olefins process to convert the methanol into at least one of ethylene and propylene. In some embodiments, the catalysts used in the methanol-to-olefins process are acidic zeolites. The zeolites are crystalline aluminosilicates with pores/cavities of molecular dimensions, including, but not limited to, ZSM-5, ZSM-35, MCM-22, SSZ-13, SAPO-34, SAPO-35, SAPO-18 and SAPO-5. In some embodiments, the reaction temperature for the methanol-to-olefins process could be from 300 to 550° C., or from 350 to 500° C. In some embodiments, the pressure could be from 0.1 to 10 atm (10.1 kPa to 1.0 MPa), or ambient atmosphere or sub-atmosphere.

In some embodiments, the method includes introducing at least a portion of the first stream into a methanol-to-gasoline process to convert the methanol into gasoline. In some embodiments, the catalysts used for the MTG process are zeolites, including, but not limited to, ZSM-5, beta zeolite, Y-zeolite, modenite and SAPO-18. In some embodiments, the reaction temperature could be from 300 to 550° C., or from 350 to 500° C. In some embodiments, the pressure could be from 1.0 to 100 atm (0.1 to 10.1 MPa), or from 1.0 to 50 atm (0.1 to 5.1 MPa).

Figure 1:
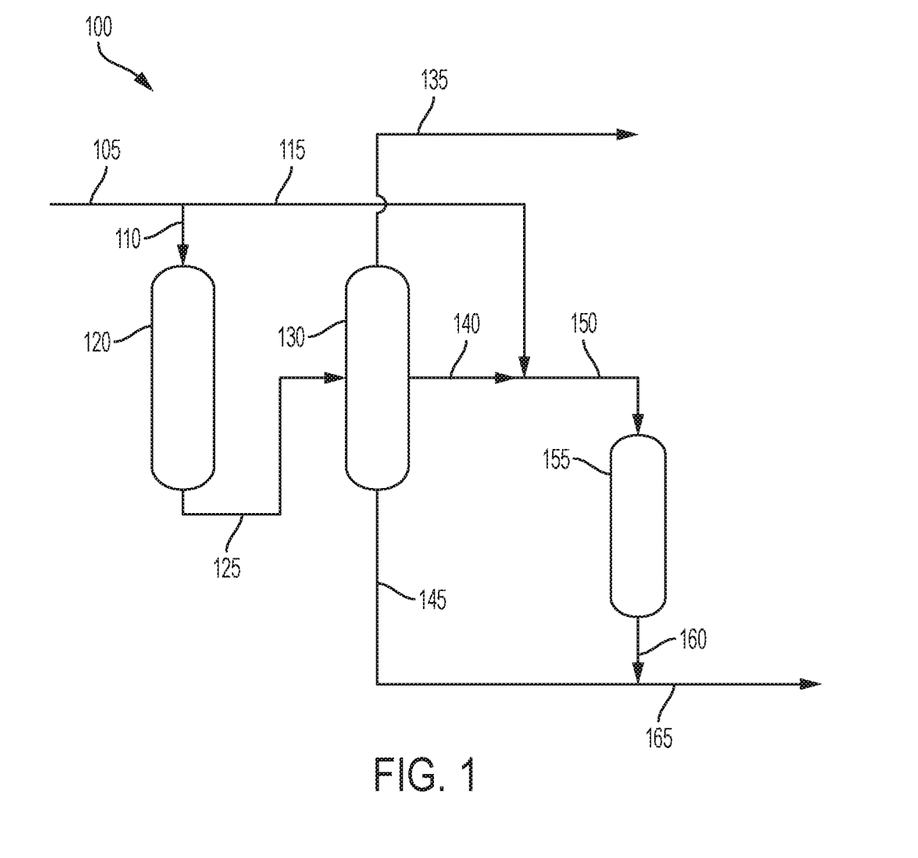
FIG. 1 illustrates one embodiment of the process of the present invention.

FIG. 1 illustrates an exemplary process 100 for a two-step isobutanol synthesis process from syngas. Syngas can be produced from the reforming or partial oxidation of natural gas and light hydrocarbons, or the gasification of coal, biomass and municipal solid waste, for example. In this process, the syngas stream 105 is split into a first portion 110 and a second portion 115. The first portion 110 passes through a first reaction zone 120 at high temperatures and high pressures in the presence of heterogeneous catalysts. The reaction temperature could range from 200 to 450° C., or from 250 to 350° C. The pressure could range from 10 to 200 atm (1.0 to 20.3 MPa), or from 50 to 150 atm (5.1 to 15.2 MPa). In addition to CO and $H_2$, $CO_2$ or inert gas, such as $N_2$ and Ar, may also be present in the syngas. The $H_2$/CO molar ratio in the syngas would typically range from 10:1 to 0.1:1; or 5:1 to 0.2:1; or 2:1 to 0.5:1.

In the first reaction zone 120, methanol, substantial amounts of ethanol and propanol, and possibly a small amount of isobutanol are formed directly from the syngas on some heterogeneous catalysts. The catalysts could include, but not limited to, Cu—Co containing catalysts, Cu—Fe containing catalysts, Cu—Ni containing catalysts, promoted Mo catalysts (e.g., $MoO_3$, $MoS_2$, MoP and $Mo_2C$) and precious metal catalysts (e.g., Rh), and combinations thereof. Suitable catalysts are described in "Synthesis of higher alcohols from syngas—recently patented catalysts and tentative ideas on the mechanism," Catalysis Today, 2 (1987) 125-170, and "Status and prospects in higher alcohols synthesis from syngas," Chem. Soc. Rev. 2017, 46, 1358-1426, which are incorporated herein by reference.

The effluent 125 from the first reaction zone 120 is sent to separation zone 130 where it is separated into a first stream 135 comprising methanol, a second stream 140 comprising ethanol and propanol, and optionally a third stream 145 comprising isobutanol (if any).

The methanol in the first stream 135 can be sent for recovery or further processing, as described below, for example.

The second stream 140 comprising ethanol and propanol can be combined with the second portion 115 of the syngas stream 105 to form combined stream 150 and sent to a second reaction zone 155. The ethanol and propanol react with the syngas in the presence of heterogeneous catalysts in the second reaction zone 155 to produce isobutanol. The catalysts could include, but not limited to, the aforementioned direct isobutanol synthesis catalysts, such as alkali and alkaline earth promoted ZnO or CuO catalysts. The reaction temperature could be from 200 to 500° C., preferably from 250 to 450° C. The pressure could be from 10 to 300 atm (1.01 to 30.4 MPa), or from 50 to 200 atm (5.1 to 20.3 MPa). This process is an aldol-condensation reaction with β-carbon addition. As discussed above, the reaction rate of the β-carbon addition is faster than that of α-carbon addition (i.e., methanol/formaldehyde-to-ethanol/acetaldehyde).

Stream 160 comprising isobutanol from the second reaction zone 155 is combined with the third stream 145 (if any) from the first reaction zone 130, and the combined product stream 165 is sent for recovery.

Figure 2:
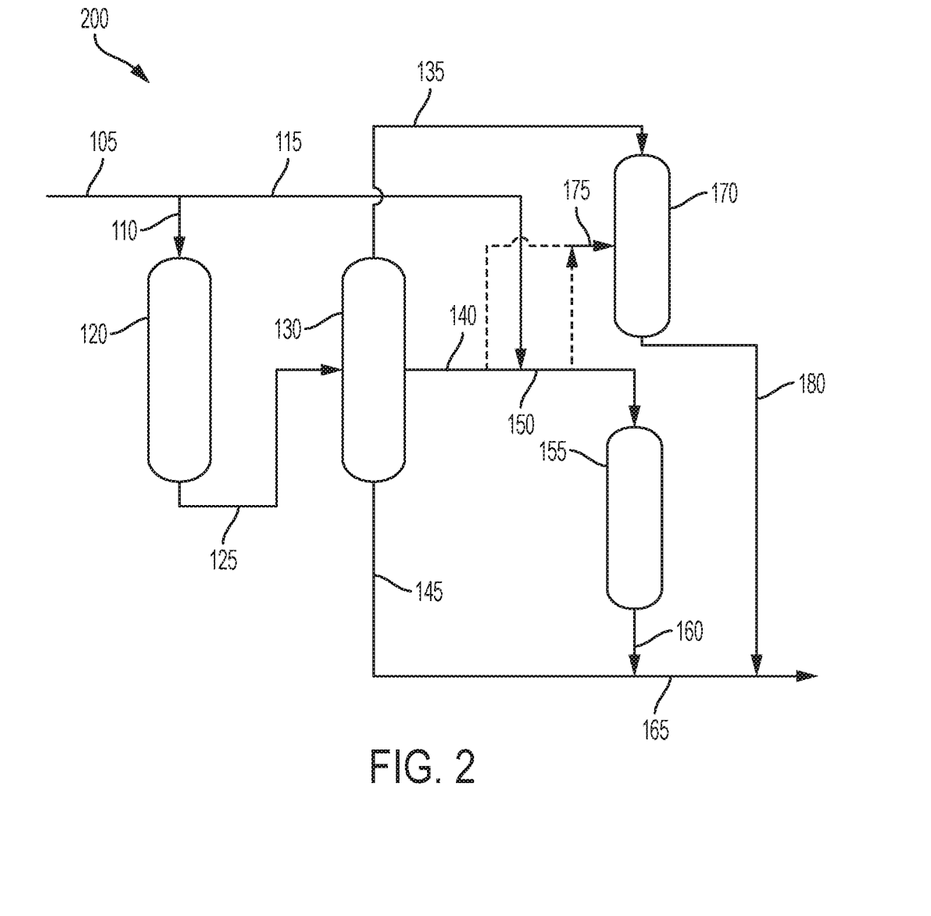
FIG. 2 illustrates another embodiment of the process of the present invention.

In the embodiment shown in FIG. 2, the first stream 135 comprising methanol is sent to a third reaction zone 170 along with stream 175 comprising ethanol and propanol. Stream 175 can comprise a portion of stream 140 comprising ethanol and propanol or a portion of combined stream 150 comprising ethanol, propanol, and syngas. Alternatively, a portion of stream 140 and a portion of stream 115 can be sent to the third reaction zone without being combined first. The ethanol and propanol react with methanol to form isobutanol through Guerbet reaction in the presence (combined stream 150) or absence (stream 140) of syngas. The Guerbet reaction is a promising method for direct conversion of lower alcohols to higher alcohols through condensation. Methanol can react with propanol to produce isobutanol through cross condensation. Ethanol can react with methanol to produce propanol, which can be further converted to isobutanol by reacting with another methanol. The presence of syngas may promote the Guerbet reaction. In this third reaction zone 170, the catalysts used may include, but are not limited to, the materials containing any elements from IA, IIA, IIIA, IV, IB, IIB and VIIIB in the periodic Table, or any catalysts summarized in "Heterogeneous catalysts for the Guerbet coupling of alcohols," ACS Catal. 2013, 3, 1588-1600, which is incorporated herein by reference. These catalysts could include, but are not limited to, MgO, MgO—$Al_2O_3$, CuO—MgO—$Al_2O_3$, CuO—CaO—$Al_2O_3$, CaO, tricalcium phosphate and alkali zeolites. The reaction temperature could be from 100 to 500° C., preferably from 150 to 400° C. The pressure could be from 1 to 300 atm (0.1 to 30.4 MPa), preferably from 1 to 100 atm (0.1 to 10.1 MPa).

Stream 180 comprising isobutanol from the third reaction zone 170 can be combined with the combined product stream 165.

Figure 3:
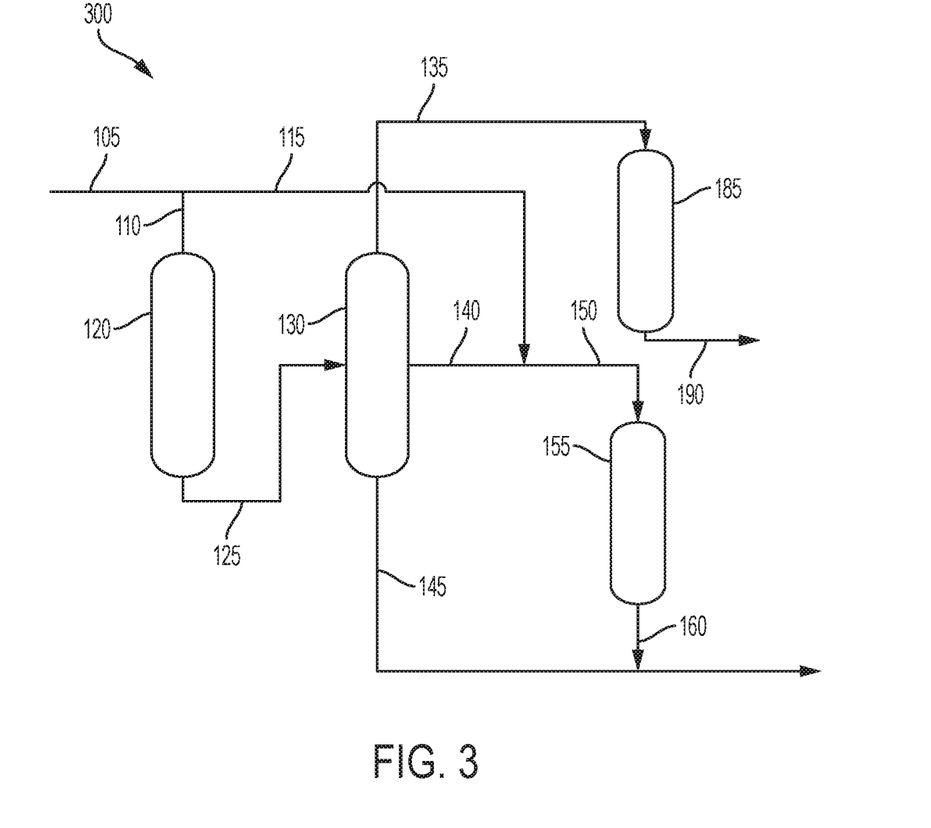
FIG. 3 illustrates another embodiment of the process of the present invention.

In another embodiment shown in FIG. 3, stream 135 comprising methanol is sent to fourth reaction zone 185. The fourth reaction zone 185 is a methanol-to-olefins (MTO) process reaction zone where the methanol is converted to ethylene and propylene. Stream 190 comprising ethylene and propylene from the fourth reaction zone 185 can be recovered. The catalysts used in the methanol-to-olefins process are acidic zeolites. The zeolites are crystalline aluminosilicates with pores/cavities of molecular dimensions, including, but not limited to, ZSM-5, ZSM-35, MCM-22, SSZ-13, SAPO-34, SAPO-35, SAPO-18 and SAPO-5. The reaction temperature could be from 300 to 550° C., preferably from 350 to 500° C. The pressure could be from 0.1 to 10 atm (10.1 kPa to 1.0 MPa), preferably ambient atmosphere or sub-atmosphere.

Figure 4:
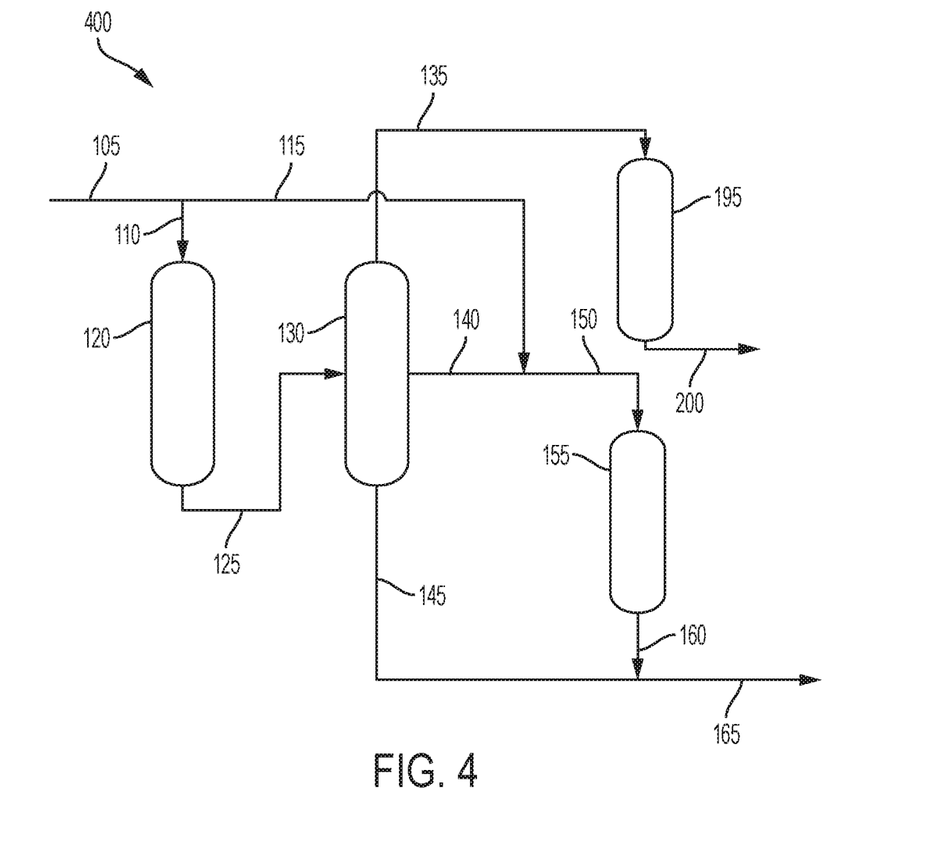
FIG. 4 illustrates another embodiment of the process of the present invention.

Alternatively, as shown in FIG. 4, stream 135 comprising methanol is sent to fifth reaction zone 195. The fifth reaction zone 195 is a methanol-to-gasoline (MTG) process reaction zone where the methanol is converted to gasoline. Stream 200 comprising gasoline from the fourth reaction zone 185 can be recovered. The catalysts used for the MTG process are zeolites, including, but not limited to, ZSM-5, beta zeolite, Y-zeolite, modenite and SAPO-18. The reaction temperature could be from 300 to 550° C., preferably from 350 to 500° C. The pressure could be from 1.0 to 100 atm (0.1 to 10.1 MPa), or from 1.0 to 50 atm (0.1 to 5.1 MPa).

In summary, a novel two-step process for producing isobutanol from syngas through the production of mixed alcohols is disclosed. This process eliminates the slowest α-carbon addition reaction in the direct isobutanol synthesis and thus improves isobutanol selectivity and yield. The syngas can be produced from reforming or partial oxidation of coal, natural gas, shale gas, biomass, biogas and municipal solid waste at high temperatures.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method of making isobutanol comprising:
  introducing a first synthesis gas stream into a first reaction zone in the presence of a first heterogeneous catalyst to produce a reaction mixture comprising a mixture of alcohols comprising methanol and a substantial amount of ethanol and propanol, wherein a weight ratio of ethanol and propanol to methanol is greater than 0.2:1 thereof;
  separating the reaction mixture into at least a first stream consisting essentially of the methanol, and a second stream consisting essentially of the ethanol and propanol; and
  introducing a second synthesis gas stream and at least a portion of the second stream into a second reaction zone in the presence of a second heterogeneous catalyst to produce isobutanol.

2. The method of claim 1 wherein the second heterogeneous catalyst comprises elements from Groups IA, IIA, IIIA, IV, IB, IIB, IIIB, VIB, VIIB, and VIIIB in the Periodic Table.

3. The method of claim 1 wherein the second heterogeneous catalyst comprises alkali and alkaline earth promoted ZnO or CuO catalysts.

4. The method of claim 1 wherein the first heterogeneous catalyst comprises one or more of Cu—Co containing catalysts, Cu—Fe containing catalysts, Cu—Ni containing catalysts, promoted Mo catalysts, and precious metal catalysts, and combinations thereof.

5. The method of claim 1 wherein the reaction mixture is separated by distillation or an adsorption desorption process.

6. The method of claim 1 wherein a molar ratio of $H_2$ to CO in the synthesis gas is in a range of 10:1 to 0.1:1.

7. The method of claim 1 further comprising:
  introducing at least a portion of the first stream and at least a portion of the second stream, and optionally a portion of the synthesis gas to a third reaction zone in the presence of a third heterogeneous catalyst to produce a second portion of isobutanol.

8. The method of claim 7 wherein the third heterogeneous catalyst comprises elements from Groups IA, IIA, IIIA, IVA, VA, IV, IB, IIB, VIB, VIIB, and VIIIB in the Periodic Table.

9. The method of claim 1 further comprising:
  introducing at least a portion of the first stream into a methanol-to-olefins process to convert the methanol into at least one of ethylene or propylene.

10. The method of claim 1 further comprising:
  introducing at least a portion of the first stream into a methanol-to-gasoline process to convert the methanol into gasoline.

11. The method of claim 1 wherein a weight ratio of ethanol and propanol to methanol is greater than 0.5:1.

12. The method of claim 1 wherein a weight ratio of ethanol and propanol to methanol is greater than 1.0:1.

13. The method of claim 1 wherein the reaction mixture further comprises isobutanol.

14. The method of claim 13 wherein separating the reaction mixture into at least the first stream comprising the methanol, and the second stream comprising the ethanol and propanol comprises separating the reaction mixture into at least the first stream comprising the methanol, the second stream comprising the ethanol and propanol, and a third stream comprising the isobutanol.

15. A method of making isobutanol comprising:
  introducing a first synthesis gas stream into a first reaction zone in the presence of a first heterogeneous catalyst to produce a reaction mixture comprising a mixture of alcohols comprising methanol and a substantial amount of ethanol and propanol, wherein a weight ratio of ethanol and propanol to methanol is greater than 0.2:1, and wherein the first heterogeneous catalyst comprises one or more of Cu—Co containing catalysts, Cu—Fe containing catalysts, Cu—Ni containing catalysts, promoted Mo catalysts, and precious metal catalysts, and combinations thereof;
  separating the reaction mixture into at least a first stream consisting essentially of the methanol, and a second stream consisting essentially of the ethanol and propanol; and
  introducing an additional synthesis gas stream and at least a portion of the second stream into a second reaction zone in the presence of a second heterogeneous catalyst to produce isobutanol, wherein the second heterogeneous catalyst comprises elements from Groups IA, IIA, IIIA, IV, IB, IIB, IIIB, VIB, VIIB, and VIIIB in the Periodic Table.

16. The method of claim 15 further comprising:
  introducing at least a portion of the first stream and at least a portion of the second stream, and optionally a portion of the synthesis gas to a third reaction zone in the presence of a third heterogeneous catalyst to produce a second portion of isobutanol, wherein the third heterogeneous catalyst comprises elements from Groups IA, IIA, IIIA, IVA, VA, IV, IB, IIB, VIB, VIIB, and VIIIB in the Periodic Table.

17. The method of claim 15 further comprising:
  introducing at least a portion of the first stream into a methanol-to-olefins process to convert the methanol into at least one of ethylene or propylene, or introducing at least a portion of the first stream into a methanol-to-gasoline process to convert the methanol into gasoline;
  or both.

18. The method of claim 15 wherein the reaction mixture further comprises isobutanol, and wherein separating the reaction mixture into at least the first stream comprising the methanol, and the second stream comprising the ethanol and propanol comprises separating the reaction mixture into at least the first stream comprising the methanol, the second stream comprising the ethanol and propanol, and a third stream comprising the isobutanol.

19. The method of claim 15 wherein a molar ratio of $H_2$ to CO in the synthesis gas is in a range of 10:1 to 0.1:1.

* * * * *